United States Patent [19]
Buckman et al.

[11] 3,942,228
[45] Mar. 9, 1976

[54] TUBING CLAMP

[76] Inventors: Thomas P. Buckman, 7804 Foothill Blvd., Sunland, Calif. 91040; Dean Vorwick, 7621 Lebesthon, Tujunga, Calif. 91042

[22] Filed: July 19, 1974

[21] Appl. No.: 490,018

[52] U.S. Cl. .............................. 24/255 SL; 251/10
[51] Int. Cl.² .......................................... F16K 7/06
[58] Field of Search..... 24/243 H, 243 LC, 243 AC, 24/248 R, 248 B, 248 E, 248 CR, 248 SL, 249 R, 249 SL, 255 C, 255 SL, 132 AA, 132 AB, 133 AC, 133 HA, 133 HL, 133 WL; 251/10

[56] References Cited
UNITED STATES PATENTS

| 823,068 | 6/1906 | Mosley | 251/10 |
|---|---|---|---|
| 3,061,263 | 10/1962 | Butler | 24/248 CR |
| 3,698,681 | 10/1972 | Lacey | 251/10 |
| 3,713,622 | 1/1973 | Dinger | 24/255 SL |
| 3,822,052 | 7/1974 | Lange | 251/10 |

*Primary Examiner*—Donald A. Griffin
*Attorney, Agent, or Firm*—Witherspoon and Lane

[57] ABSTRACT

A clamp adapted for mounting on a flexible tube to control flow therethrough, said clamp having a pair of parallel legs connected by a spring element whereby the legs may swing toward and away from each other, a flexible catch arm on one leg having a catch adapted to engage a latch on the other arm, cooperating cam means on the catch arm and latch to swing the catch arm away from the latch upon movement of the latch carrying leg toward the other leg whereby the catch is cleared by the latch which allows the catch arm to swing toward the latch and engage same to retain the legs in close position, this movement causing confronting clamping elements on the legs to compress the tubing therebetween to close off flow. Openings are provided in the catch arm and spring element to frictionally receive the flexible tube and retain the clamp on the tube thereby.

4 Claims, 5 Drawing Figures

U.S. Patent  March 9, 1976  3,942,228
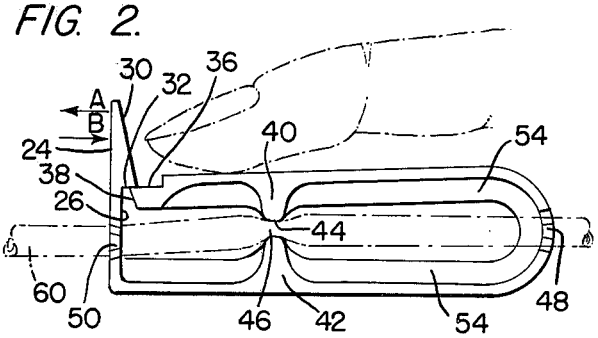
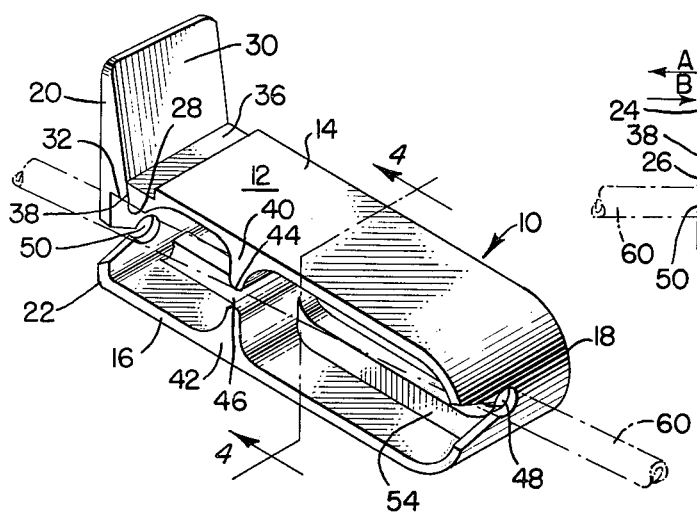
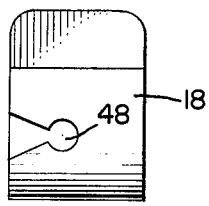
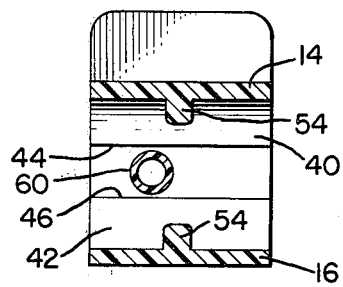
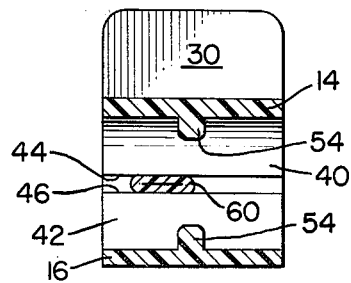

TUBING CLAMP

SUMMARY OF THE INVENTION

This invention relates to a clamp for flexible tubing wherein means are provided on the clamp for easily installing the clamp on the tubing and retaining same thereon.

There are many clamps in use today on flexible tubing which adequately control flow, but lack other desirable features relating to handling of the clamp. It is with these deficiencies in mind that the clamping device of this invention has been developed.

It is an object of this invention to provide a clamp which may be easily installed on and retained on flexible tubing.

It is another object of this invention to provide a clamp having a spring latch-catch arrangement which may be readily operated by one hand.

It is a still further object of the invention to provide a clamp for flexible tubing which is dependable and inexpensive to manufacture.

The above and other objects will become more apparent when taken in conjunction with the following detailed description and drawing illustrating a preferred embodiment of the invention.

IN THE DRAWING

FIG. 1 is a perspective view of the tubing clamp with the tubing shown in phantom, FIG. 2 is a side elevational view of the clamp illustrating the cut-off position, FIG. 3 is an end view showing the opening which frictionally retains the tubing, FIG. 4 is a cross sectional view taken along line 4—4 of FIG. 1 illustrating the clamp in open position, and FIG. 5 is a cross sectional view similar to FIG. 4 wherein the clamp has compressed the tubing to close off fluid flow.

DETAILED DESCRIPTION OF THE INVENTION

As best illustrated in FIGS. 1 and 2, the tubing clamp 10 comprises a body 12 which is U-shaped in cross section and has generally parallel upper and lower legs 14 and 16 connected by a curved hose portion 18. A flexible catch arm 20 extends vertically from the end 22 of the lower body leg 16 to a point well above the upper body leg 14. The flexible catch arm 20 has an outer planar face 24 and an inner face 26. A catch 28 is formed on the inner face 26 by downwardly and outwardly sloping catch arm cam face 30 intersecting catch face 32 extending perpendicularly outward from the inner face 26 of catch arm 20.

The upper body leg 14 is made flexible by the nature of the curved base portion 18 so that it may swing toward and away from the lower body leg 16. The end of the lower leg 16 is provided with a latch portion 36 having a sloping outer face 38 conforming in slope to that of the catch arm cam face 30. The length of the upper leg 14 is such that the outer face 38 of the latch portion 36 will bear against catch arm cam face 30 with the catch arm in a generally perpendicular attitude with respect to the lower leg 16.

Upper body leg 14 is provided with a clamping element 40 midway its extremities; similarly the lower body leg 16 is provided with a comforming clamping element 42 in alignment with clamping element 40. It should be noted that in the at rest or storage or full flow position the confronting faces 44 and 46 of the clamping elements 40 and 42 are spaced apart so that they merely engage the flexible tubing 60 passing therebetween. The at rest or full flow positions of the clamp is illustrated in FIG. 1.

The curved hose portion 18 is formed with a side opening 48 sized to frictionally engage the flexible tubing 60 adapted for positioning thereon. Similarly, the catch arm 20 is provided with a side opening 50 generally in alignment with the space between the clamping elements 40 and 42 and the other side opening 48. Here again, side opening 50 is sized so as to frictionally engage the flexible tubing 60 carried thereon.

In order to furnish the body 12 with the requisite strength a longitudinal centrally positioned ridge portion 54 extends along the confronting faces of the body legs 14 and 16 and the inside of the base portion 18.

As will be readily apparent the clamp of this invention is susceptible of many uses, even so the basic concept and use is the same. In use, the clamp 10 is positioned on a flexible tube 60 by introducing the tube into the side openings 48 and 50 and between the clamping elements 40 and 42 as shown in FIG. 1. The side openings are sized to frictionally grip the tube without appreciable diminishing of the flow passage at that point. The holding friction should be sufficient so that the clamp will remain in place on the tube without any additional holding features.

When it is decided to stop flow through tube 60, the upper leg 14 is pressed toward the lower leg 16 whereby the cam face 38 on the latch 36 engages cam face 30 to cause the catch arm 20 to swing outwardly as indicated by the arrow A. As soon as the entire latch cam face 38 clears the catch face 32, the catch arm 20 will swing in the direction indicated by arrow B so that the latch 36 will engage the catch 32 to retain the clamp in the closed, no flow position, with clamping elements 40 and 42 engaging the tube 60 as shown in FIG. 5. In order to release the clamp, the catch arm 20 is moved in the direction of arrow A (FIG. 2) so that the latch 36 clears the catch 32 and the clamping elements 40 and 42 move away from each other to assume the position illustrated in FIG. 4.

The fact that the entire positioning of the clamp on the tube, as well as the clamping and unclamping can be done with one hand adds much utility to the device, particularly in connection with intravenous units.

The clamp may be made from any material having the required strength and flexibility. Obviously, plastics are most useful since they possess such qualities and are easy to work.

We claim:

1. A clamp adapted for mounting on flexible tubing, by means of a single hand, said tubing being positioned between clamping elements which control flow through the tubing, said clamp comprising a body, U-shaped in cross section, having generally parallel upper and lower legs connected by a curved base portion, aligned tubing clamping elements extending upwardly from the lower body legs and downwardly from the upper body leg intermediate the length of said legs, a flexible catch arm extending upwardly from the free end of the lower leg and projecting beyond the upper leg, a catch member on the catch arm facing the upper leg extremity, a latch on the free end of the upper body leg with its end surface in engagement with the confronting face on the catch arm, cooperating cam surfaces on the engaging portions of the latch and catch arm whereby movement of the upper body leg toward the lower body leg causes the catch arm to be cammed outwardly away from the latch so that the latch may proceed downwardly below the catch whereupon the catch arm swings toward the latch so that the catch engages the latch and the tubing positioned between the clamping elements is compressed to prevent flow therethrough, and the curved base portion having a tube receiving opening and a slot providing communication between said opening and the outside edge of the base portion said opening being aligned with the space between the clamping elements and the catch arm having a tube receiving opening and a slot providing communication between said catch arm opening and the outside edge of the catch arm, said catch arm opening being aligned with the opening in the curved base portion, said slots being aligned and adapted to receive and pass the flexible tubing into the aforesaid tube receiving openings.

2. The invention as set forth in claim 1 and wherein there is a space between the clamping elements when the clamp is in at rest position, said tubing passing through the space between the clamping elements.

3. The invention as set forth in claim 2 and wherein the openings are sized to frictionally engage the flexible tubing so that the clamp will be positively held on the tubing.

4. The invention as set forth in claim 3 and wherein there is a reinforcing rib running centrally on the confronting faces of the upper and lower legs and the curved base portions to provide requisite strength.

* * * * *